(12) United States Patent
Jadhav et al.

(10) Patent No.: US 9,987,073 B2
(45) Date of Patent: Jun. 5, 2018

(54) ELECTROSURGICAL COAGULATION INSTRUMENT INCLUDING A SUCTION PIPE AND A COLLAPSIBLE TIP

(71) Applicant: COVIDIEN LP, Mansfield, MA (US)

(72) Inventors: Amarsinh D. Jadhav, Islampur-Dist-Sangli (IN); Nikhil P. Mankar, Pune (IN)

(73) Assignee: COVIDIEN LP, Mansfield, MA (US)

( * ) Notice: Subject to any disclaimer, the term of this patent is extended or adjusted under 35 U.S.C. 154(b) by 775 days.

(21) Appl. No.: 14/521,690

(22) Filed: Oct. 23, 2014

(65) Prior Publication Data

US 2015/0141990 A1    May 21, 2015

Related U.S. Application Data

(60) Provisional application No. 61/906,026, filed on Nov. 19, 2013, provisional application No. 61/906,140, filed on Nov. 19, 2013.

(51) Int. Cl.
*A61B 18/14* (2006.01)
*A61B 18/00* (2006.01)

(52) U.S. Cl.
CPC .......... *A61B 18/14* (2013.01); *A61B 18/1477* (2013.01); *A61B 18/1487* (2013.01); *A61B 2018/00029* (2013.01); *A61B 2018/00196* (2013.01); *A61B 2018/00214* (2013.01); *A61B 2018/00589* (2013.01);
(Continued)

(58) Field of Classification Search
CPC . A61B 18/14; A61B 18/1487; A61B 18/1477; A61B 2218/002; A61B 2018/00601; A61B 2018/00964; A61B 2018/00029; A61B 2018/00589; A61B 2018/1475; A61B 2018/1422; A61B 2018/00958; A61B 2018/00946
See application file for complete search history.

(56) References Cited

U.S. PATENT DOCUMENTS 3,720,896 A * 3/1973 Beierlein ............... A61B 18/14
                                                    335/206
D330,253 S    10/1992 Burek
(Continued)

FOREIGN PATENT DOCUMENTS

CN    1088419 A    6/1994
DE    2429021 A1   1/1976
(Continued)

OTHER PUBLICATIONS

Chinese Office Action dated May 30, 2016, issued in Chinese Application No. 201410655276.3.
(Continued)

*Primary Examiner* — Rex R Holmes

(57) ABSTRACT

An electrosurgical coagulation instrument includes a body, a suction pipe, and an electrode. The body has a central passage that defines a longitudinal axis. The suction pipe has a distal end and defines a lumen. The suction pipe is disposed within the central passage. The electrode has a distal tip that is configured to deliver energy to tissue. The electrode is disposed within the lumen of the suction pipe. The suction pipe and/or the electrode is slidable along the longitudinal axis with respect to the body and the other of the electrode and the suction pipe.

12 Claims, 8 Drawing Sheets

(52) U.S. Cl.
CPC ............ *A61B 2018/00601* (2013.01); *A61B 2018/00607* (2013.01); *A61B 2018/00946* (2013.01); *A61B 2018/00958* (2013.01); *A61B 2018/00964* (2013.01); *A61B 2018/1422* (2013.01); *A61B 2018/1427* (2013.01); *A61B 2018/1475* (2013.01); *A61B 2218/002* (2013.01); *A61B 2218/007* (2013.01)

(56) References Cited

U.S. PATENT DOCUMENTS

| | | | |
|---|---|---|---|
| 5,665,102 | A | 9/1997 | Yoon |
| 6,197,024 | B1 | 3/2001 | Sullivan |
| 6,231,591 | B1 | 5/2001 | Desai |
| 6,293,945 | B1 * | 9/2001 | Parins ................ A61B 18/1402 606/45 |
| 7,147,635 | B2 | 12/2006 | Ciarrocca |
| 7,198,625 | B1 | 4/2007 | Hui et al. |
| 7,537,594 | B2 | 5/2009 | Sartor |
| 7,749,221 | B2 | 7/2010 | Rontal |
| 2009/0171274 | A1 | 7/2009 | Harlev et al. |
| 2012/0016397 | A1 | 1/2012 | Briganti et al. |
| 2012/0203223 | A1 | 8/2012 | Terry et al. |
| 2013/0296843 | A1 | 11/2013 | Boudreaux et al. |

FOREIGN PATENT DOCUMENTS

| | | |
|---|---|---|
| DE | 2460481 A1 | 6/1976 |
| DE | 3045996 A1 | 7/1982 |
| DE | 3710489 A1 | 11/1987 |
| DE | 4139029 A1 | 6/1993 |
| DE | 4326037 A1 | 2/1995 |
| DE | 9117019.2 | 4/1995 |
| DE | 19537897 A1 | 3/1997 |
| DE | 9117299 U1 | 3/2000 |
| DE | 19848784 A1 | 5/2000 |
| DE | 29724247 U1 | 8/2000 |
| EP | 0787485 A2 | 8/1997 |
| EP | 0956827 A1 | 11/1999 |
| EP | 1090598 A1 | 4/2001 |
| EP | 1602337 A1 | 12/2005 |
| FR | 1340509 A | 10/1963 |
| FR | 2 235 669 A1 | 1/1975 |
| FR | 2926974 A1 | 8/2009 |
| GB | 2452392 A | 3/2009 |
| JP | 61-159953 A | 7/1986 |
| JP | 4441492 B2 | 3/2010 |
| SU | 1438745 A1 | 11/1988 |
| WO | 03061499 A1 | 7/2003 |
| WO | 2004/045436 A1 | 6/2004 |

OTHER PUBLICATIONS

Partial European Search Report dated Mar. 27, 2015, issued in European Appln. No. 14193429.
Brand et al. "Electrosurgical Debulking of Ovarian Cancer: A New Technique Using the Argon Beam Coagulator" Gynecologic Oncology 39.
Farin et al. "Technology of Argon Plasma . . . Endoscopic Applications" Endoscopic Surgery and Allied Technologies, No. 1, vol. 2, pp. 71-77 (Feb. 1994).
Grund et al., "Endoscopic Argon Plasma . . . Flexible Endoscopy" Surgery and Allied Technologies, No. 1, vol. 2, pp. 42-46 (Feb. 1994).
Hernandez et al. "A Controlled Study of the Argon Beam Coagulator for Partial Nephrectomy" The Journal of Urology, vol. 143, May (J.Urol. 143: 1062-1065, 1990).
Mark H. Mellow, "The Role of Endoscopic Laser Therapy in Gastrointestinal Neoplasms" Advanced Therapeutic Endoscopy, pp. 17-21.
Silverstein et al., "Thermal Coagulation Therapy for Upper Gastrointestinal Bleeding" Advanced Therapeutic Endoscopy, pp. 79-84.
Valleylab in the OR; Tonsillectomy Article; Aug. 2005.
Valleylab Suction Coagulators; May 2009.
Ward et al. "A Significant New Contribution to Radical Head and Neck Surgery" Arch Otolaryngol Head Neck Surg., vol. 115, Aug. 1989 pp. 921-923.
Waye et al., "Techniques in Therapeutic Endoscopy", W.B.Saunders Company, Philadelphia, PA., pp. 1.7-1.15.
U.S. Appl. No. 13/741,171, filed Jan. 14, 2013; inventor: Huseman.
U.S. Appl. No. 13/741,181, filed Jan. 14, 2013; inventor: Huseman.
U.S. Appl. No. 14/456,832, filed Aug. 11, 2014; inventor: Heard.
U.S. Appl. No. 14/521,746, filed Oct. 23, 2014; inventor: Amarsinh D. Jadhav.
European Office Action dated Nov. 10, 2017 in EP Application No. 14 193 429.

* cited by examiner

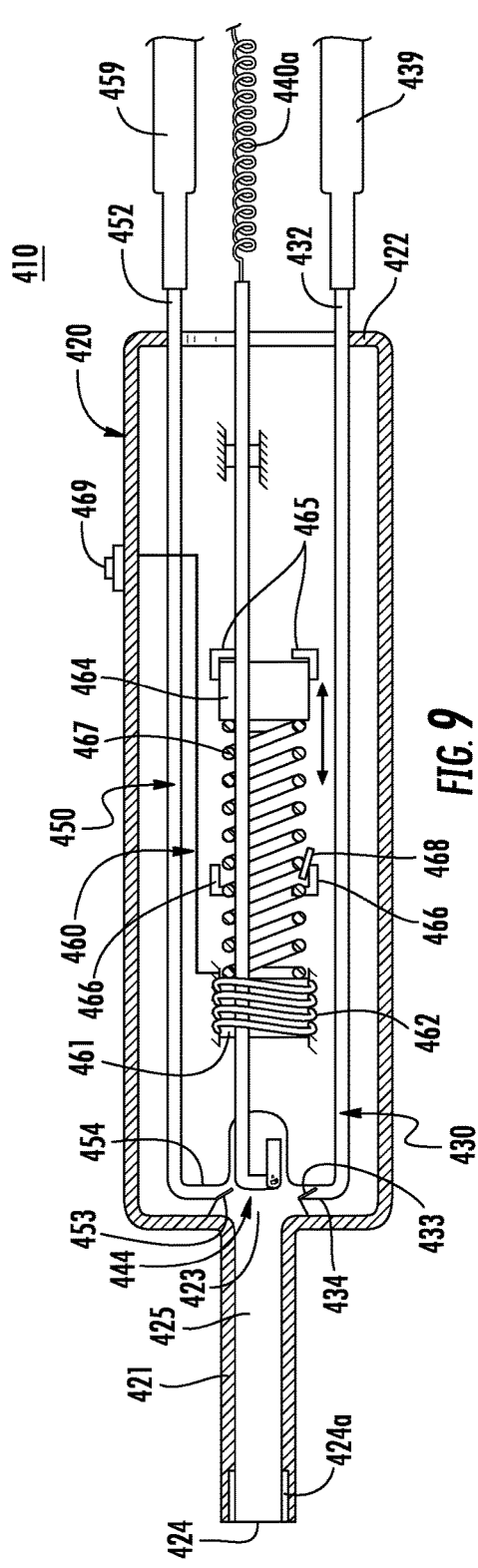
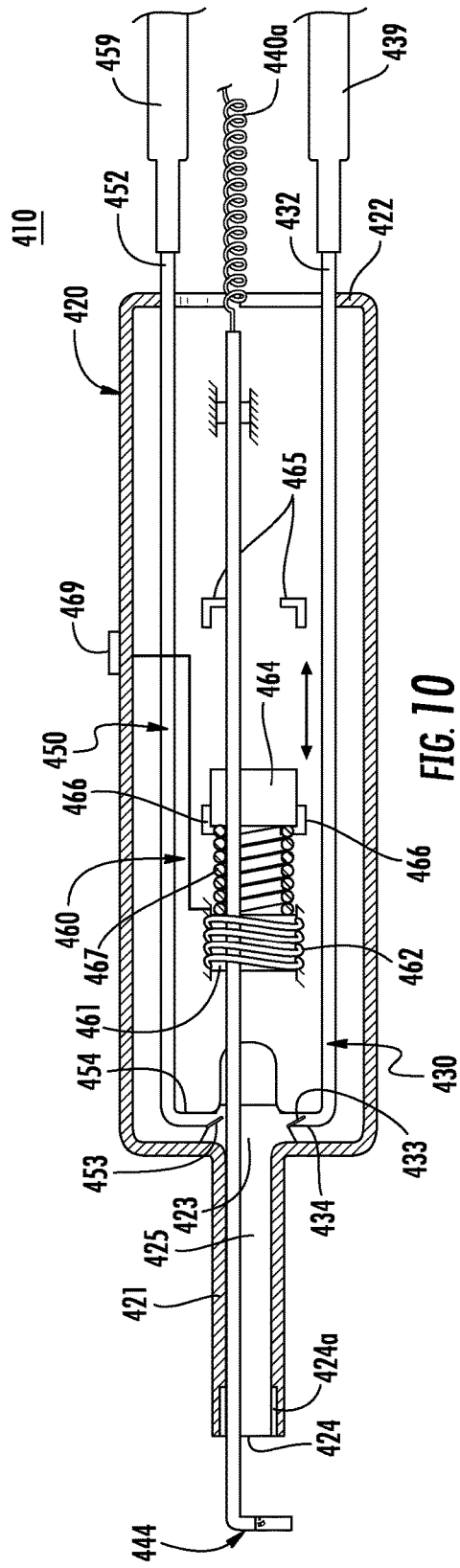

ELECTROSURGICAL COAGULATION INSTRUMENT INCLUDING A SUCTION PIPE AND A COLLAPSIBLE TIP

CROSS-REFERENCE TO RELATED APPLICATIONS

This application claims the benefit of, and priority to, U.S. Provisional Patent Application Nos. 61/906,026 and 61/906,140, both of which were filed on Nov. 19, 2013. This application is related to U.S. patent application Ser. No. 14/521,746 filed on Oct. 23, 2014. The entire contents of each of the above applications are hereby incorporated herein by reference.

BACKGROUND

1. Technical Field

The present disclosure relates to surgical instruments and, more specifically, to surgical instruments including retractable and/or collapsible electrodes for treating, e.g., dissecting and/or coagulating, tissue.

2. Discussion of Related Art

The coagulation of bleeding blood vessels and tissue using electrically conductive suction tubes typically includes a combination of electrocautery and a suction device that is employed in surgery wherever excessive blood must be removed from the bleeding site in order to facilitate hemostasis of any bleeding vessels. More particularly, during certain surgical procedure, several layers of tissue must be penetrated to reach the operative field. When excising an organ, such as a gallbladder, the tissue surrounding the organ must often be penetrated and dissected before the organ can be removed. The tissues being dissected, however, often contain blood vessels, nerves, lymph vessels, and the like. The technique of blunt dissection is often used to prevent unnecessary damage caused by severing these vessels or nerves.

Blunt dissection, as opposed to sharp dissection, involves the use of a blunt surface to break through the tissue, thereby preventing the damage and bleeding caused by lasers and scalpels, the tools of sharp dissection. Hard surgical sponges, generally known as peanuts or Kittner sponges, or a surgeon's fingers are often used as blunt dissectors. A peanut is a tightly wound ball of absorbent material, such as gauze or other woven cotton, which is typically gripped with forceps and acts to abrade the tissue being dissected so that the dissection can be performed by either pulling on the tissue or by forcing the peanut through the tissue.

Laparoscopy, surgery performed through several small incisions or openings in the body rather than through a single large opening reduces the trauma and the risk of infection as compared to normal, open surgical procedures. The use of conventional blunt dissectors, such as the peanut, during laparoscopic procedures becomes difficult. For instance, peanuts, being secured only by forceps, can become loose in the body. Further, the view of the operative field often becomes obstructed by pieces of tissue, blood, and other bodily fluids produced during blunt dissection, necessitating the immediate need for both irrigation and aspiration of the operative field. Thus, the dissection must be stopped, the dissector must be removed, and an irrigator and/or aspirator must be inserted to remove the fluid and debris.

Electrosurgical suction coagulators which both coagulate and dissect tissue generally include a conductive suction tube having an insulating coating over all but a most distal portion of the tube so that the distal portion forms a generally annular ablating electrode. The distal end can be used as a blunt dissection device and/or a blunt coagulator. A suction source is attached to a proximal portion of the tube for evacuating excess fluid and debris from the surgical site through the distal end of the tube.

SUMMARY

In accordance with the present disclosure, an electrosurgical coagulation instrument is provided including a body, a suction pipe, and an electrode. The body has a central passage that defines a longitudinal axis. The suction pipe has a distal end and defines a lumen. The suction pipe is disposed within the central passage. The electrode has a distal tip that is configured to deliver energy to tissue. The electrode is disposed within the lumen of the suction pipe. The suction pipe and/or the electrode is slidable along the longitudinal axis with respect to the body and the other of the electrode and the suction pipe.

In aspects of the present disclosure, the suction pipe is operatively associated with a suction pipe actuating member and a suction pipe biasing member. The suction pipe biasing member is configured to urge the suction pipe proximally. the suction pipe actuation member selectively actuatable to move the suction pipe distally against the bias of the suction pipe biasing member. The suction pipe can have a retracted position and a deployed position. In the retracted position, the distal end of the suction pipe is proximal to a distal end of the body. In the deployed position, the distal end of the suction pipe is distal to the distal end of the body. The electrode can be longitudinally fixed relative to the body with the distal tip of the electrode extending from the distal end of the body and the distal end of the suction pipe positioned distal to the distal tip of the electrode when the suction pipe is in the deployed position.

In some aspects of the present disclosure, the electrode is operatively associated with an electrode actuation member and an electrode biasing member. The electrode biasing member is configured to urge the electrode proximally. the electrode actuating member is selectively actuatable to move the electrode distally against the electrode biasing member. The electrode can have a withdrawn position and an extended position. In the withdrawn position, a distal tip of the electrode is proximal to a distal end of the suction pipe. In the extended position, the distal tip of the electrode is distal to the distal end of the suction pipe. The suction pipe can be longitudinally fixed relative to the body.

The distal tip of the electrode can have a first position corresponding to the extended position of the electrode and a second position corresponding to the withdrawn position of the electrode. In the first position, the distal tip extends radially outwardly beyond the outer dimension of the suction pipe. In the second position, the distal tip is positioned within the lumen of the suction pipe.

Also provided in accordance with the present disclosure is an electrosurgical coagulation instrument including a body, a suction pipe, and an electrode. The body includes a nose positioned at a distal end of the body. The nose includes a central passage that defines a longitudinal axis. The suction pipe has a distal end and is disposed within the body. The electrode has a distal tip. The electrode is disposed within the body and configured to deliver energy to tissue. the electrode is slidable along the longitudinal axis with respect to the body. The electrode has a withdrawn position and an extended position. In the withdrawn position, the distal tip of the electrode is positioned within the body proximal to the distal end of the body. In the extended position, a portion of the distal tip of the electrode extends distally from the distal end of the body.

In aspects of the present disclosure, the distal tip includes a fixed portion and a collapsible portion. The distal tip has a first position and a second position corresponding to the withdrawn position and the extended position of the electrode respectively. In the first position, the collapsible portion is disposed within the radial dimension of the central passage of the body. In the second position, the collapsible portion extends beyond the radial dimensions of the central passage of the body. The fixed portion can include a pivot pin. The collapsible portion can include a cam slot and a cam pin positioned within the cam slot. The cam pin is configured to move within the cam slot to move the collapsible portion from the first position to the second position. The instrument can include a pull link that is coupled to the cam pin. The pull link being configured to move the cam pin within the cam slot to move the collapsible portion from the first position to the second position when the electrode approaches the extended position. The instrument can include a tip biasing member that is positioned about the pivot pin. The tip biasing member being configured to urge the collapsible portion towards the first position.

In another aspect of the present disclosure, the instrument includes an actuation assembly having a fixed magnet, a sliding magnet, and an inductive coil. The inductive coil is positioned about the fixed magnet. The sliding magnet is slidable along the longitudinal axis of the body and is coupled to the electrode. When the inductive is energized, the fixed magnet attracts the sliding magnet such that the sliding magnet slides distally and extends the electrode. The actuation assembly can include a magnet biasing member that urges the sliding magnet proximally. the actuation assembly can include proximal and distal stops configured to limit the longitudinal movement of the sliding magnet. The distal stop can include a mechanical activation switch configured to activate the electrode when the sliding magnet is adjacent the distal stop.

In yet another aspect of the present disclosure, the body includes a chamber positioned at a proximal end of the central passage. The chamber in fluid connection with the distal end of the body. The instrument can further include an irrigation pipe having a distal end. the distal ends of the suction pipe and the irrigation pipe positioned at and in fluid connection with the chamber. The distal end of the suction pipe can include a directional valve configured to permit fluid to flow from the chamber to the suction pipe and configured to inhibit fluid from flowing from the suction pipe to the chamber. The distal end of the irrigation pipe can include a directional valve configured to permit fluid to flow from the irrigation pipe to the chamber and configured to inhibit fluid from flowing from the chamber to the irrigation pipe.

Methods of treating tissue provided in accordance with the present disclosure include extending a distal tip of an electrode of a surgical instrument from a body of the surgical instrument to expose the distal tip by sliding the electrode along a longitudinal axis defined by the body, delivering energy from the distal tip to tissue, and applying suction adjacent the distal end of the body with a suction pipe of the surgical instrument.

In aspects of the present disclosure, delivering energy from the distal tip to tissue and applying suction adjacent the distal end of the body are performed simultaneously. The method may include retracting the distal tip of the electrode into the body before applying suction adjacent the distal end of the body. The method may include irrigating adjacent the distal end of the body with a fluid exiting through a nose of the body. The method may include concealing the distal tip of the electrode from the second position back to the first position after delivering energy from the distal tip to tissue and before applying suction adjacent the distal end of the body.

In aspects of the present disclosure, the surgical instrument includes an actuation assembly that includes an inductive coil. Extending the distal tip of the electrode may include energizing the inductive coil to effect sliding of the electrode. The actuation assembly may also include a mechanical activation switch and a sliding magnet. The sliding magnet may be disposed within the inductive coil and engaged to the electrode. In embodiments, delivering energy from the distal tip to tissue includes engaging the mechanical activation switch with the sliding magnet to energize the electrode.

In aspects of the present disclosure, extending the distal tip of the electrode includes extending a portion of the distal tip from a first position to a second position. In the first position, the distal tip is disposed within an outer radial dimension of a distal end of the body and in the second position, the portion of the distal tip extends beyond the outer radial dimension.

In aspects of the present disclosure, the distal tip of the electrode may include a collapsible portion. Extending the distal tip of the electrode may include moving the collapsible portion to extend beyond an outer radial dimension of a nose of the surgical instrument. The method may include retracting the distal tip of the electrode within the body such that the portion of the collapsible portion is returned to within the outer radial dimension of the nose.

In yet another aspect of the present disclosure, a method of treating tissue includes exposing a distal tip of an electrode of a surgical instrument from a first position to a second position, delivering energy from the distal tip to tissue, and applying suction with the suction pipe adjacent the distal end of the body. In the first position, the distal tip is disposed within a lumen of the suction pipe of the surgical instrument and in the second position, the distal tip of the electrode extends from the distal end of the suction pipe.

In aspects of the present disclosure, exposing the distal tip of the electrode from the first position to the second position includes retracting the suction pipe from about the distal tip of the electrode. The method may include extending the suction pipe about the distal tip of the electrode after delivering energy from the distal tip to tissue and before applying suction adjacent the distal end of the suction pipe.

In aspects of the present disclosure, exposing the distal tip of the electrode from the first position to the second position includes extending a portion of the electrode beyond an outer dimension of the distal end of the suction pipe. In the second position, the distal tip of the electrode may extend beyond an outer radial dimension of the distal end of the suction pipe.

By providing a surgical instrument including a collapsible distal tip the electrode of the instrument can have an activatible tip with a surface area larger than the outer dimension of the suction pipe and or the access port used to access the body cavity. This may provide a clinician the ability to quickly dissect and coagulate tissue reducing the time required to complete a surgical procedure.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein:

FIG. 9 is a cross-sectional view of still another electrosurgical coagulation instrument in accordance with the present disclosure with the electrode in the withdrawn position;

FIG. 10 is a cross-sectional view of the instrument of FIG. 9 with the electrode in the extended position;

DETAILED DESCRIPTION

Figure 1A:
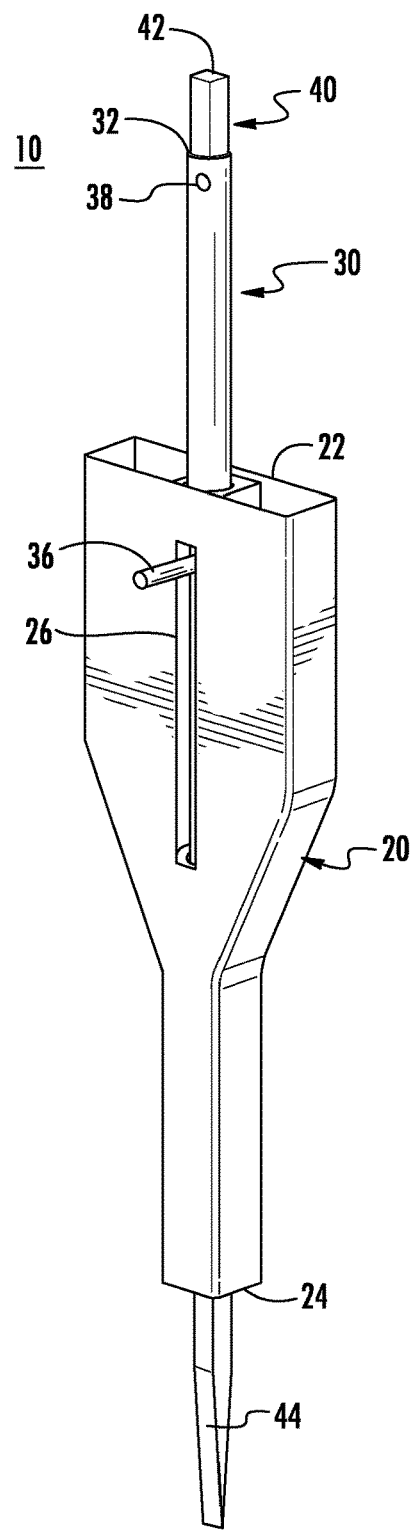
FIGS. 1A and 1B are perspective and cross-sectional views, respectively, of a electrosurgical coagulation instrument in accordance with the present disclosure with the suction pipe in the retracted position.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closest to the clinician and the term "distal" will refer to the portion of the device or component thereof that is furthest from the clinician.

Figure 1B:
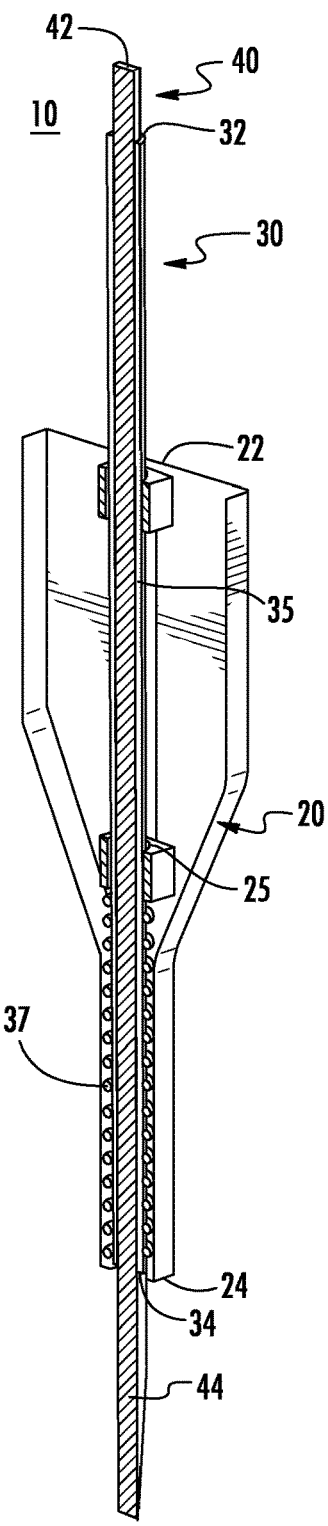

Referring now to FIGS. 1A and 1B, an electrosurgical coagulation surgical instrument 10 is provided in accordance with the present disclosure incorporating a body 20, an extendable suction pipe 30, and an electrode 40. Body 20 includes a proximal end 22, a distal end 24, and a central passage 25 extending between the proximal and distal ends 22, 24. In embodiments, body 20 includes a longitudinal slot 26 extending through body 20 and into central passage 25.

Suction pipe 30 includes a proximal end 32, a suction tip or distal end 34, and a lumen 35 extending between proximal and distal ends 32, 24. Suction pipe 30 is slidably positioned within central passage 25 of body 20. Suction pipe 30 is operatively associated with a suction device (not shown) by a suction port 38. In embodiments, a suction pipe biasing member 37 is disposed about the outer surface of suction pipe 30 within body 20. Suction pipe biasing member 37 urges suction pipe 30 proximally towards a retracted position. In some embodiments, a suction pipe actuating member 36 is coupled to the outer surface of suction pipe 30 and extends through longitudinal slot 26 to permit deployment of suction pipe 30. In certain embodiments, distal end 34 of suction pipe 30 includes a plurality of holes 34a configured to improve suction (see FIGS. 2A and 2B). Suction pipe 30 is configured to suction fluids through distal end 34 with the fluids exiting suction pipe 30 through suction port 38.

Electrode 40 includes a proximal end 42 and a distal tip 44. Electrode 40 is disposed within lumen 35 of suction pipe 30 and is longitudinally fixed relative to body 20. Electrode 40 is operatively associated with an energy source (not shown). In embodiments, proximal end 42 of electrode 40 is connected to the energy source. The energy source is configured to provide energy that is delivered to tissue through electrode 40. Electrode 40 can be configured as a monopolar electrode, a bipolar electrode, a microwave electrode, an ultrasonic blade, etc.

Electrode 40 has an activated state and an inactivate state. In the activated state, the energy source provides energy to electrode 40 enabling electrode 40 to deliver the energy to tissue to dissect and coagulate tissue at distal tip 44. In the inactivate state, energy is not delivered to tissue through distal tip 44 of electrode 40. It will be appreciated that as energy is delivered to tissue through distal tip 44, distal tip 44 can increase in temperature. Instrument 10 can include an activation button (not shown) for selectively supplying energy to electrode 40 or may be configured to automatically supply energy to electrode 40 when suction pipe 30 is retracted.

Figure 2A:
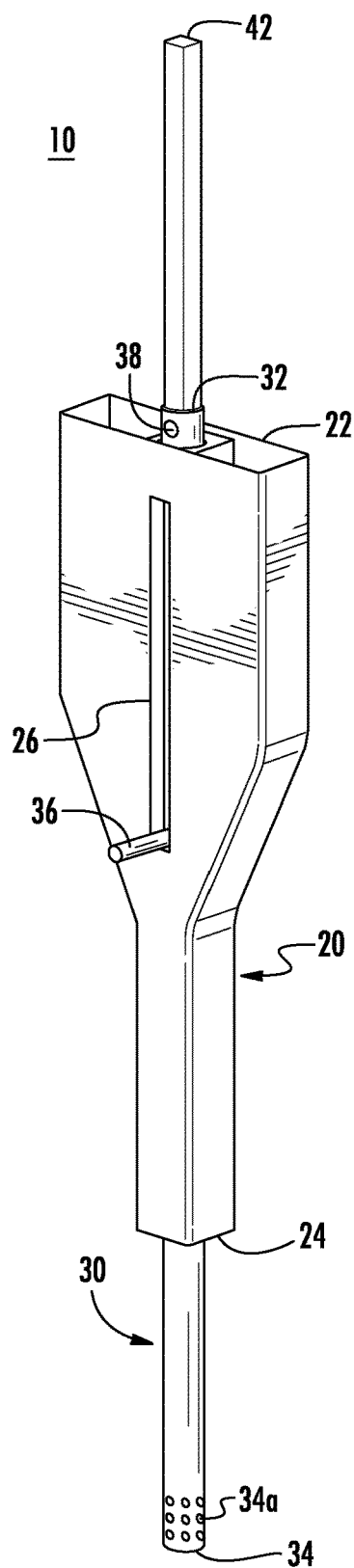
FIGS. 2A and 2B are perspective and cross-sectional views, respectively, of the instrument of FIGS. 1A and 1B with the suction pipe in the deployed position.
Figure 2B:
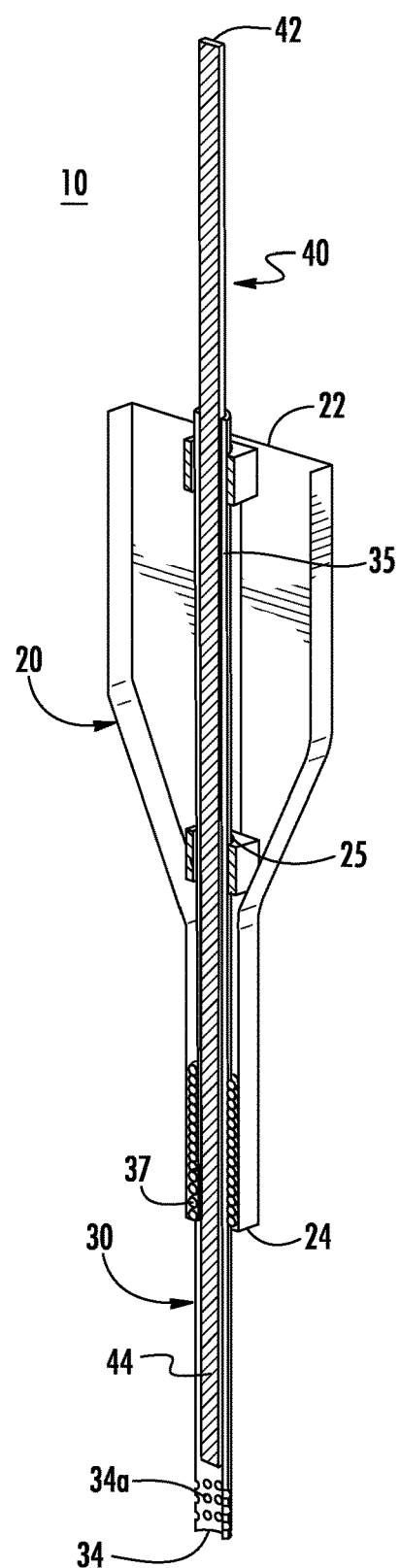

With additional reference to FIGS. 2A and 2B, suction pipe 30 has a retracted position (FIGS. 1A and 1B) and a deployed position (FIGS. 2A and 2B). In the retracted position, distal end 34 of suction pipe 30 is near distal end 24 of body 20. In some embodiments, distal end 34 of suction pipe 30 is proximal to distal end 24 of body 20 when suction pipe 30 is in the retracted position. In the deployed position, distal end 34 of suction pipe 30 is extended past distal tip 44 of electrode 40. In some embodiments, suction pipe actuation member 36 is moved distally to extend suction pipe 30 against suction pipe biasing member 37. In certain embodiments, the length of longitudinal slot 26 defines the range of longitudinal movement of suction pipe 30 between the retracted position and the deployed position by interacting with suction pipe actuation member 36, i.e., the proximal and distal ends of longitudinal slot 26 function as stops defining the extent of longitudinal movement of suction pipe 30. Suction pipe 30 is configured to provide suction in its retracted position and/or in its deployed position.

Figure 3A:
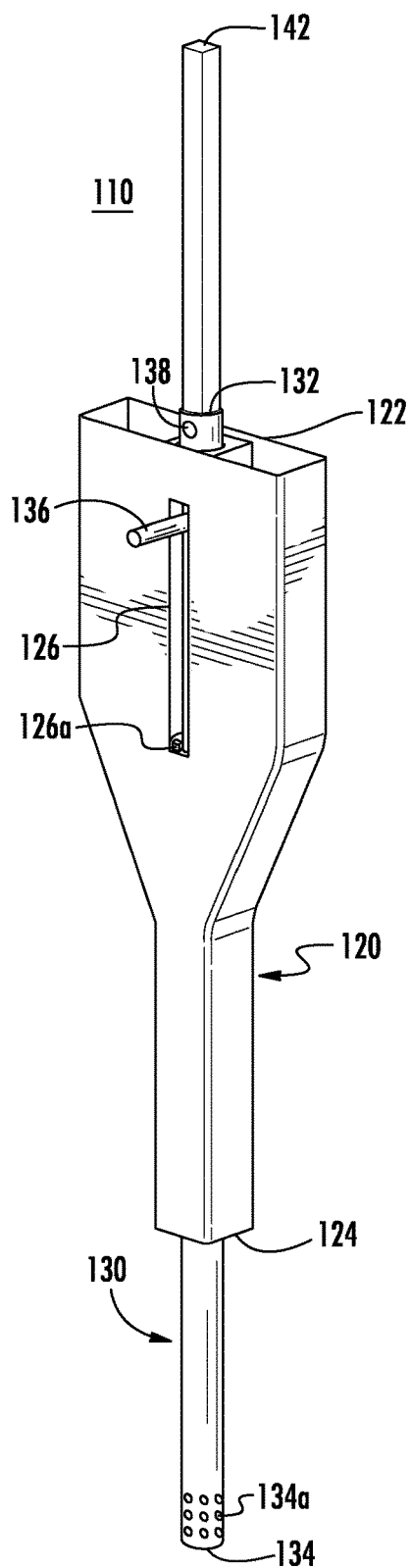
FIGS. 3A and 3B are perspective and cross-sectional views, respectively, of another electrosurgical coagulation instrument in accordance with the present disclosure with the electrode in the withdrawn position.
Figure 3B:
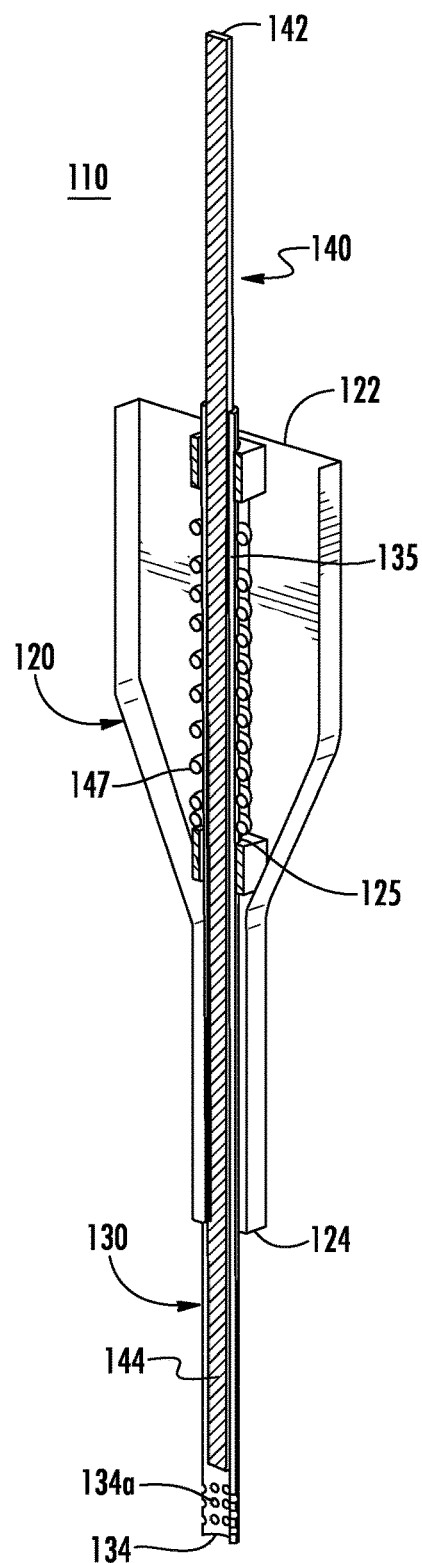

Referring now to FIGS. 3A and 3B, another electrosurgical coagulation surgical instrument 110 is provided in accordance with the present disclosure incorporating a body 120, a suction pipe 130, and an extendable electrode 140. Body 120 is substantially similar to body 20 and includes a proximal end 122, a distal end 124, and a central passage 125 extending between the proximal and distal ends 122, 124. In embodiments, body 120 includes a longitudinal slot 126 extending through body 120 and into central passage 125.

Suction pipe 130 includes a proximal end 132, a distal end 134, and a lumen 135 extending between proximal and distal ends 132, 134. Suction pipe 130 is longitudinally fixed relative to body 120 within central passage 125 of body 120 such that distal end 134 of suction pipe 130 extends proximally from distal end 124 of body 120. Suction pipe 130 is operatively associated with a suction device (not shown) by a suction port 138. In embodiments, distal end 134 of suction pipe 130 includes a plurality of holes 134a configured to improve suction. Suction pipe 130 is configured to suction fluids through distal end 134 with the fluids exiting suction pipe 130 from suction port 138.

Electrode 140 includes a proximal end 142 and a distal tip 144. Electrode is slidably disposed within lumen 135 of suction pipe 130. Electrode tip 140 is operatively associated with an energy source (not shown). In embodiments, proximal end 142 of electrode is connected to the energy source. Electrode 140 is configured to dissect and coagulate tissue by delivering energy to tissue near or in contact with distal tip 144. In embodiments, an electrode biasing member 147 is disposed about the outer surface of suction pipe 130 within body 120. Electrode biasing member 147 urges electrode 140 proximally. In some embodiments, an electrode actuating member 146 is coupled to the outer surface of electrode 140 and extends through longitudinal slot 126. In certain embodiments, electrode biasing member 147 engages electrode actuation member 146 to urge electrode 140 proximally. Electrode 140 has an activated state and an inactivate state similar to electrode 40 discussed above, as such only the differences will be discussed in detail below.

Figure 4A:
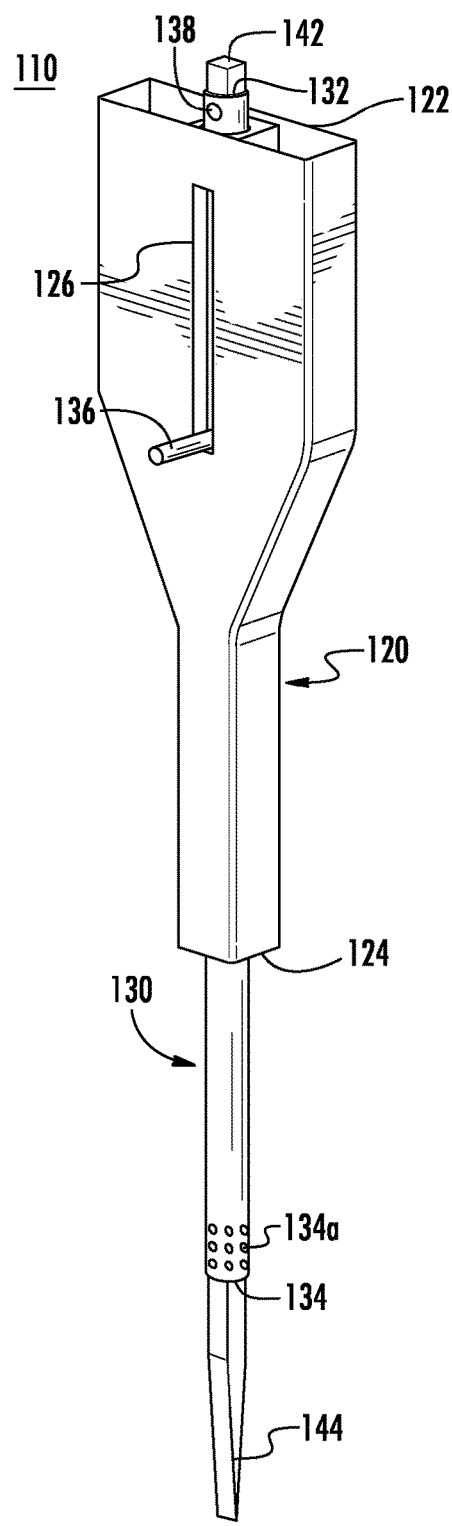
FIGS. 4A and 4B are perspective and cross-sectional views, respectively, of the instrument of FIGS. 3A and 3B with the electrode in the extended position.
Figure 4B:
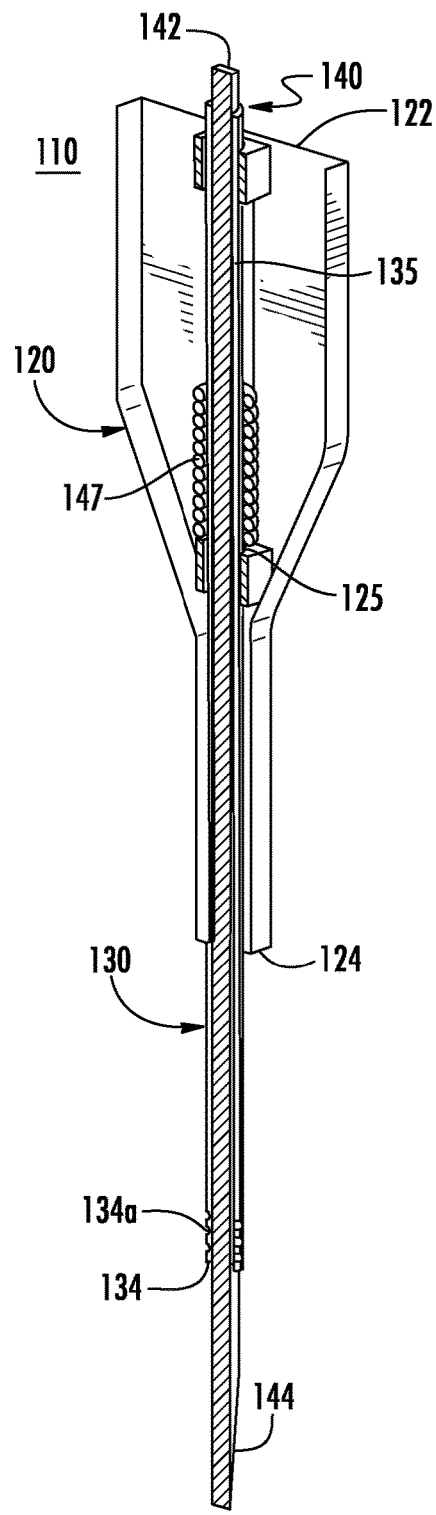

With additional reference to FIGS. 4A and 4B, electrode 140 has a withdrawn position (FIGS. 3A and 3B) and an extended position (FIGS. 4A and 4B). In the withdrawn position, distal tip 144 of electrode 140 is proximal to distal end 134 of suction pipe 130. In the extended position, distal tip 144 of electrode 140 extended such that distal tip 144 is positioned distally of distal end 134 of suction pipe 130 and is free to contact tissue. In embodiments, electrode actuating member 146 is moved distally to extend electrode 140 against electrode biasing member 147, e.g., suction pipe 130 can include a slot (not shown) permitting electrode biasing member 147 to engage electrode 140. In some embodiments, longitudinal slot 126 of body 120 defines the range of longitudinal movement of electrode 140 between the withdrawn position and the extended position by interacting with electrode actuation member 146, i.e. the proximal and distal ends of longitudinal slot 126 function as stops defining the amount of longitudinal movement of electrode 140. In certain embodiments, electrode 140 is activatable only in the extended position. In particular embodiments, the distal end of longitudinal slot 126 includes an activation switch 126a which is engaged by electrode actuation member 146 when electrode actuation member 146 approaches the distal end of longitudinal slot 126. Activation switch 126a can be a contact switch, a push button switch, a micro switch, a lever switch, etc.

Figure 5:
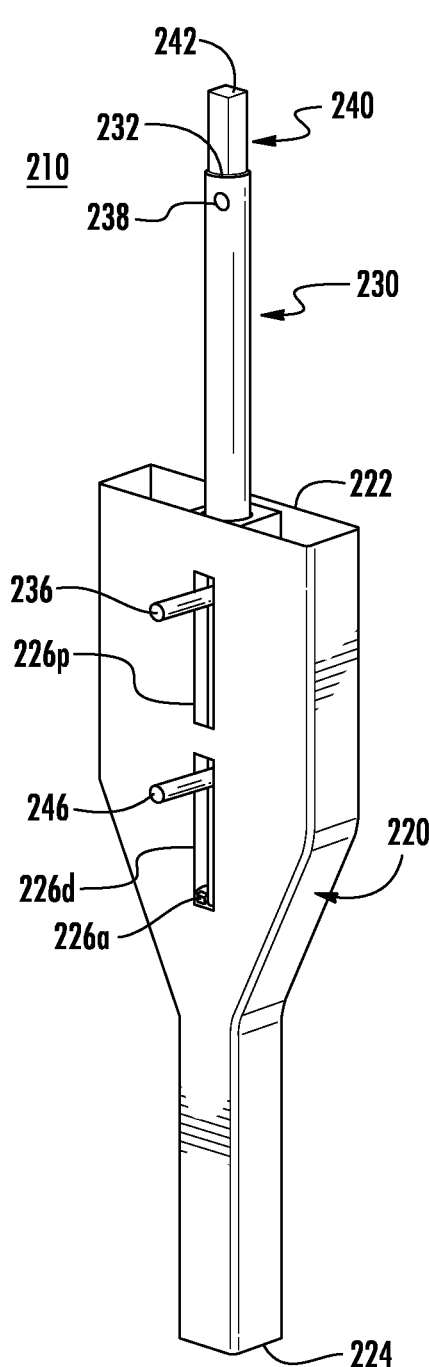
FIG. 5 is a perspective view of yet another electrosurgical coagulation instrument in accordance with the present disclosure with the suction pipe in the retracted position and the electrode in the withdrawn position.
Figure 6:
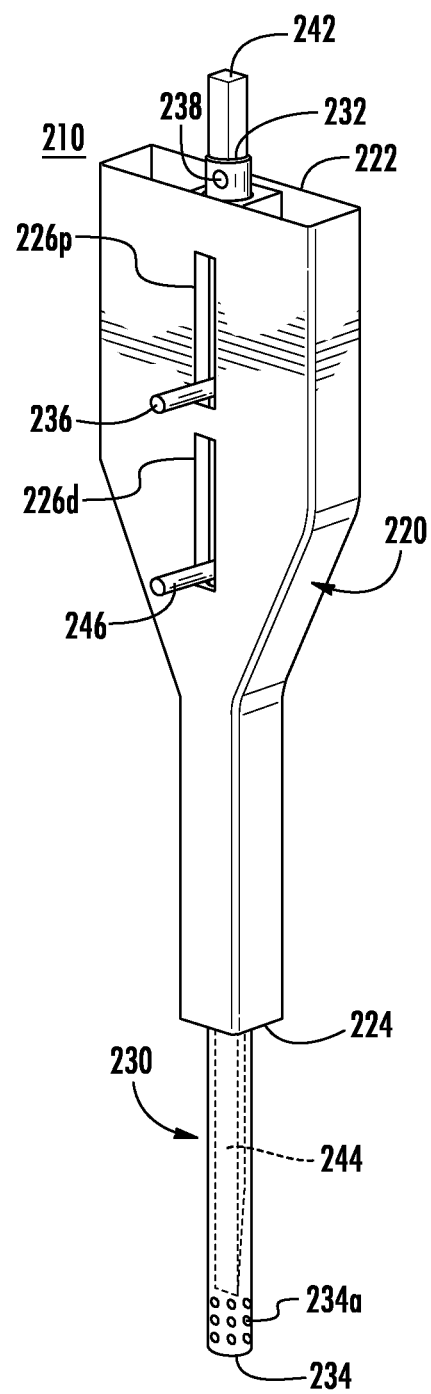
FIG. 6 is a perspective view of the instrument of FIG. 5 with the suction pipe in the deployed position and the electrode in the extended position.

Referring to FIGS. 5 and 6, yet another electrosurgical coagulation surgical instrument 210 is provided in accordance with the present disclosure incorporating a body 220, an extendable suction pipe 230, and an extendable electrode 240. Body 220 is substantially similar to body 20 and includes a proximal end 222, a distal end 224, and a central passage (not shown) extending between the proximal and distal ends 222, 224. In embodiments, body 220 includes two longitudinal slots 226p, 226d extending through body 220 and into the central passage.

Suction pipe 230 is substantially similar to suction pipe 30 of instrument 10 and includes proximal and distal ends 232, 234 and a lumen (not shown) extending between proximal and distal ends 232, 224. Suction pipe 230 is slidably positioned within the central passage of body 220. Suction pipe 230 is operatively associated with a suction device (not shown) by a suction port 238. In embodiments, a suction pipe biasing member (not shown) is disposed about the outer surface of suction pipe 230 within body 220. The suction pipe biasing member urges suction pipe 230 proximally. In some embodiments, a suction pipe actuating member 236 is disposed about the outer surface of suction pipe 230 and extends through longitudinal slot 226p to engage suction pipe 230. In certain embodiments, distal end 234 of suction pipe 230 includes a plurality of holes configured to improve suction. Suction pipe 230 is configured to suction fluids through distal end 234 with the fluids exiting suction pipe 230 through suction port 238.

Electrode 240 is substantially similar to electrode 140 and includes a proximal end 242 and a distal tip 244. Electrode 240 is slidably disposed within lumen 235 of suction pipe 230. Electrode tip 244 is operatively associated with an energy source (not shown). In embodiments, proximal end 242 of electrode 240 is connected to the energy source. Electrode 240 is configured to dissect and coagulate tissue by delivering energy to tissue through distal tip 244. In embodiments, an electrode biasing member (not shown) is disposed about the outer surface of suction pipe 230 within body 220. The electrode biasing member urges electrode 240 proximally. The electrode biasing member (not shown) can be positioned distal to the suction pipe biasing member (not shown). In some embodiments, an electrode actuating member 246 is coupled to the outer surface of electrode 240 and extends through the other longitudinal slot 226d. In certain embodiments, the electrode biasing member engages electrode actuating member 246 to urge electrode 240 proximally. Electrode 240 has an activated state and an inactivate state similar to electrode 40 discussed above, as such only the differences will be discussed in detail below.

Suction pipe 230 has a retracted position and a deployed position similar to suction pipe 30. Electrode 240 has a withdrawn position and an extended position similar to electrode 140, as such only the differences will be discussed. Suction pipe 230 and electrode 240 are selectably and independently movable relative to body 220.

Figure 7:
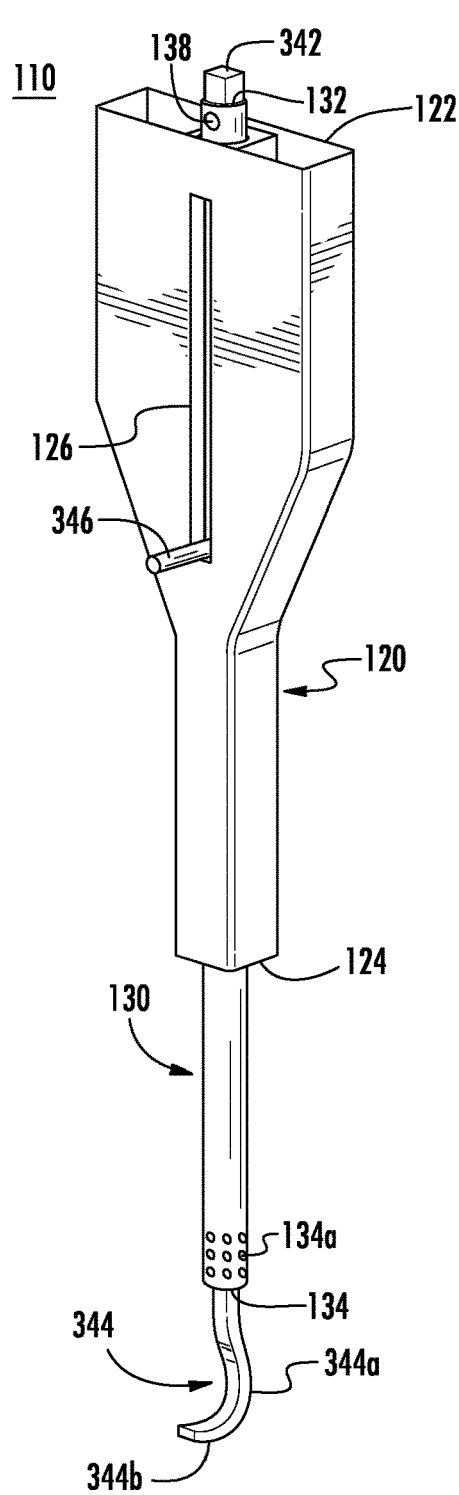
FIG. 7 is a perspective view of the instrument of FIG. 3 incorporating another electrode in the extended position in accordance with the present disclosure.
Figure 8:
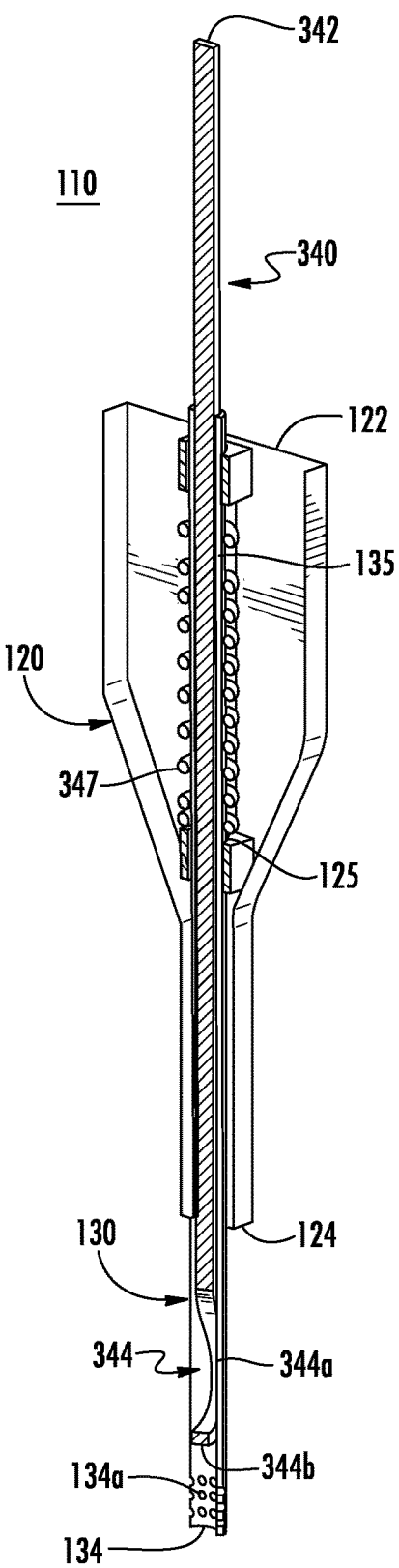
FIG. 8 is a cross-sectional view of the instrument of FIG. 7 with the electrode in the withdrawn position.

Referring to FIGS. 7 and 8, another electrode 340 is provided in accordance with the present disclosure incorporating a proximal end 342 and a collapsible distal tip 344. Electrode 340 is similar to electrodes 40, 140, and 240, as such only the differences will be discussed in detail below. Electrode 340 is shown in use with instrument 110 but it will be appreciated that electrode 340 can also be used with instruments 10 and 210 as an alternative to electrodes 40 and 240, respectively, or with any other suitable surgical instrument.

Collapsible distal tip 344 of electrode 340 includes a proximal portion 344a and a distal portion 344b. Collapsible distal tip 344 is biased towards a second position (FIG. 7) such that when collapsible distal tip 344 is positioned distal to distal end 134 of suction pipe 130, distal portion 344b extends beyond the dimensions of the outer surface of suction pipe 130, i.e., distal portion 344b crosses the longitudinal axis of instrument 110 and extends for a length greater than the radius of suction pipe 130 along an axis orthogonal to the longitudinal axis of instrument 110. In some embodiments when in the second position, distal portion 344b extends along an axis orthogonal to the longitudinal axis of instrument 110 beyond the outer surface of both sides of suction pipe 130 such that the length of distal portion 344b is greater than the diameter of suction pipe 130.

Collapsible distal tip 344 also has a first position (FIG. 8) when collapsible distal tip 344 is positioned proximal to the distal end 134 of suction pipe 130 and within suction pipe 130, e.g., when confined within suction pipe 130. When in the first position, the inner surface of suction pipe 130 interacts with collapsible distal tip 344 to constrain distal tip 344 in the first position such that distal portion 344b is within lumen 135, e.g., within the outer dimensions of suction pipe 130, as shown in FIG. 8. Electrode 340 can be constructed of a material having a resilient bias towards the second position or may be formed from a shape-memory material such as Nitnol.

Referring to FIGS. 9-12, yet another electrosurgical coagulation instrument 410 provided in accordance with the present disclosure incorporates a body 420, a suction pipe 430, an electrode 440, an irrigation pipe 450, and an actuation assembly 460. Body 420 includes a suction tip or nose 421, a proximal end 422, a chamber 423, a distal end 424, and a central passage 425. Body 420 can be constructed from a biocompatible plastic material or other suitable material. Central passage 425 is disposed within nose 421 and fluidly connects chamber 423 and distal end 424. Distal end 424 can include a metal insert or sleeve 424a positioned in an inner surface of distal end 424. Metal insert 424a can be configured to protect plastic body 420 from damage by a heated distal tip assembly 444, although the insert can be constructed of any material suitable to protect plastic body 420 from a heated distal tip assembly 444. Chamber 423 forms a fluid seal at the proximal end of central passage 425.

Suction pipe 430 has a proximal end 432 and a distal end 434. Distal end 434 is fluidly coupled to chamber 423 through a valve 433. Valve 433 can be a directional valve permitting fluid to flow from chamber 423 into suction pipe 430. In embodiments, proximal end 432 of suction pipe 430 is connected to a vacuum source 439 that is configured to draw fluid from chamber 423.

Irrigation pipe 450 has a proximal end 452 and a distal end 434. Distal end 434 is fluidly coupled to chamber 423 through a valve 453. Valve 453 can be a directional valve permitting fluid to flow from irrigation pipe 450 into chamber 423. In embodiments, proximal end 452 of irrigation pipe 450 is connected to an irrigation source 459 that provides fluid for irrigation pipe 450.

Figure 11:
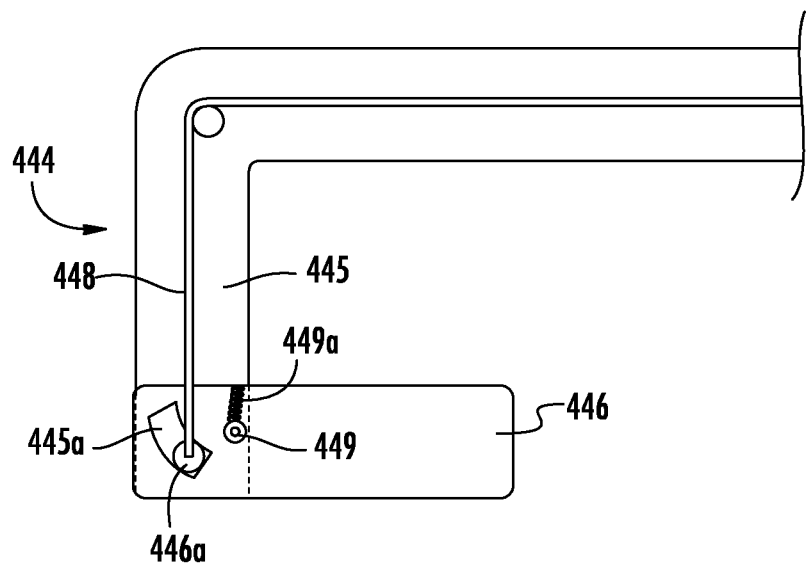
FIG. 11 is an enlarged cross-sectional view of the distal tip assembly of the instrument of FIG. 9 in the withdrawn condition.
Figure 12:
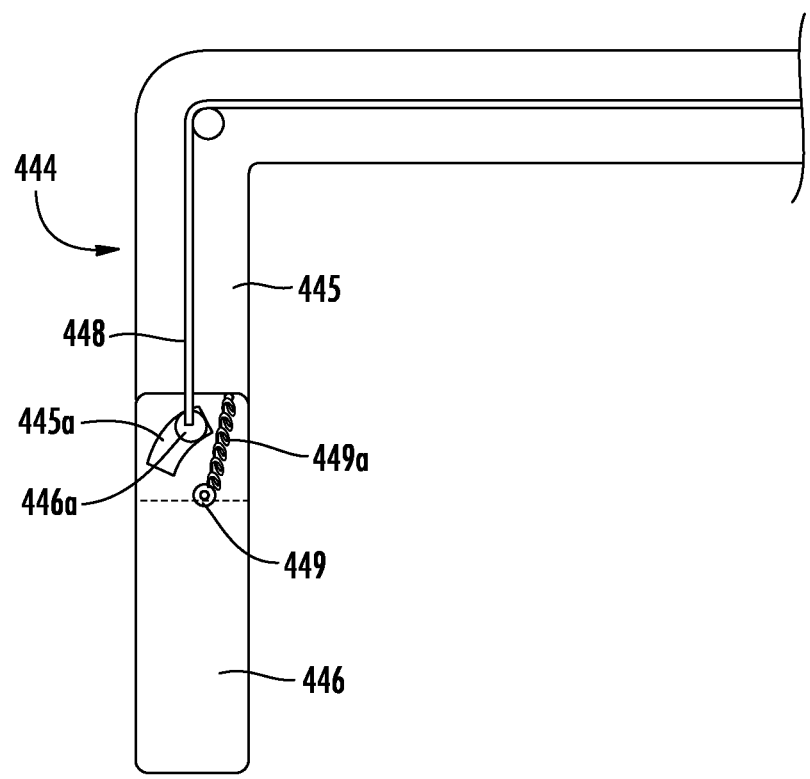
FIG. 12 is an enlarged cross-sectional view of the distal tip assembly of the instrument of FIG. 9 in the extended condition.

Electrode 440 includes a proximal end 442 and a distal tip assembly 444. Distal tip assembly 444 includes a fixed portion 445, a collapsible portion 446, and a pivot pin 449 as shown in FIGS. 11 and 12. Distal tip assembly 444 can define various configurations, i.e., straight, curved, angled, etc. Fixed portion 445 has a cam slot 445a. Collapsible portion 446 is pivotally coupled to fixed portion 445 by pivot pin 449 and includes a cam pin 446a slidably positioned within cam slot 445a of fixed portion 445. A pull link 448 is coupled to cam pin 446a to move cam pin 446a within cam slot 445a and is configured to extend collapsible portion 446 as discussed in detail below. Alternatively, electrode 440 may employ the features of electrode 340 (FIGS. 7 and 8).

Electrode 440 has a withdrawn position (FIG. 9) and an extended position (FIG. 10). In the withdrawn position, distal tip assembly 444 is positioned within chamber 423 and in the extended position distal tip assembly 444 is positioned beyond distal end 424 of body 420. Actuation assembly 460 is configured to move electrode 440 from the withdrawn position to the extended position.

Actuation assembly 460 includes a fixed magnet 461, an inductive coil 462, a sliding magnet 464, and an actuation button 469. Fixed magnet 461 is positioned distal of sliding magnet 464. Actuation button 469 is electrically coupled to inductive coil 462 to energize inductive coil 462. Inductive coil 462 is position about fixed magnet 461 and configured to control the magnetic field of fixed magnet 461 when energized as discussed below. Sliding magnet 464 is coupled to electrode 440 such that electrode 440 cooperates with longitudinal movement of sliding magnet 464. Electrode 440 can pass through an opening or slot in fixed magnet 461 such that fixed magnet 461 does not interfere with the longitudinal movement of electrode 440. Sliding magnet 464 is positioned between proximal stops 465 and distal stops 466. A magnet biasing member 467 is supported on fixed magnet 461 and configured to urge sliding magnet 464 proximally. Distal stops 466 can include a mechanical activation switch 468 that is configured to energize electrode 440. Mechanical activation switch 466 can be a plunger, a cantilever switch, a contact switch, etc.

When inductive coil 462 is energized, inductive coil 462 induces the magnetic field of fixed magnet 461 to attract sliding magnet 464 distally towards fixed magnet 461 and against magnet biasing member 467. As sliding magnet 464 moves distally, electrode cooperates with sliding magnet 464 to extend distal tip assembly 444 distally beyond distal end 424 of body 420. Distal stops 466 are positioned such that sliding magnet 461 contacts distal stops after distal tip assembly 444 extends from distal end 424 of body 420. When distal stops 466 include mechanical activation switch 468, sliding magnet 464 engages mechanical activation switch 468 to energize electrode 440 only when distal tip assembly 444 extends beyond distal end 424. Moreover, if an external force moves electrode 440 proximally, sliding magnet can disengage mechanical activation switch 468, for example, electrode 440 could be pressed against tissue and moved proximally relative to body 420.

Collapsible portion 446 has a first position (FIG. 11) and a second position (FIG. 12). A tip biasing member 449a is positioned on pivot pin 449 to urge collapsible portion 446 towards the first position. Tip biasing member 449a can be a torsion spring. When collapsible portion 446 is in the first position, distal tip 444 is within the dimensions of central passage 425 of nose 421. Pull link 448 is configured to move collapsible portion 446 to the second position, against tip biasing member 449a, when electrode 440 is in the second position by moving cam pin 446a within cam slot 445a. When collapsible portion 446 is in the second position a portion of distal tip assembly 444 is beyond the outer dimension of nose 421 as shown in FIG. 12. In embodiments, collapsible portion 446 automatically moves to the second position when distal tip assembly 444 is extended beyond distal end 424 of body 420. In certain embodiments, pull link 448 automatically moves cam pin 446a within cam slot 445a when distal tip assembly 444 approaches the extended position and is beyond distal end 424 of body 420.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the claimed invention. Therefore, the above description should not be construed as limiting, but merely as exemplifications of particular embodiments. Those skilled in the art will envision other modifications within the scope and spirit of the claims appended hereto.

What is claimed:

1. An electrosurgical coagulation instrument comprising:
a body having a central passage defining a longitudinal axis and a longitudinal slot defined in an outer surface of the body;
an activation switch fixed within the longitudinal slot of the body;
a suction pipe having a distal end and defining a lumen therethrough, the suction pipe disposed within the central passage; and
an electrode having a distal tip configured to deliver energy to tissue, the electrode disposed within the lumen of the suction pipe, wherein at least one of the suction pipe and the electrode is slidable along the longitudinal axis with respect to the body and the other of the electrode and the suction pipe, the at least one of the suction pipe and the electrode operably coupled to an actuating member, the actuating member disposed within the longitudinal slot of the body such that the actuating member is configured to engage the activation switch to activate delivery of energy from the electrode to tissue.

2. The instrument of claim 1, wherein the suction pipe is operatively associated with the actuating member and a suction pipe biasing member, the suction pipe biasing member configured to urge the suction pipe proximally, the actuating member selectively actuatable to move the suction pipe distally against the bias of the suction pipe biasing member.

3. The instrument of claim 2, wherein in a retracted position of the suction pipe the distal end of the suction pipe is proximal to a distal end of the body and in a deployed position of the suction pipe the distal end of the suction pipe is distal to the distal end of the body.

4. The instrument of claim 3, wherein the electrode is longitudinally fixed and positioned with the distal end of the suction pipe that extends from the distal end of the body, the distal end of the suction pipe positioned distal to the distal tip of the electrode when the suction pipe is in the deployed position.

5. The instrument of claim 1, wherein the electrode is operatively associated with the actuating member and an electrode biasing member, the electrode biasing member configured to urge the electrode proximally, the actuating member selectively actuatable to move the electrode distally against the electrode biasing member.

6. The instrument of claim 5, wherein in a withdrawn position of the electrode, the distal tip of the electrode is proximal to a distal end of the suction pipe and in an extended position of the electrode the distal tip of the electrode is distal to the distal end of the suction pipe.

7. The instrument of claim 6, wherein the suction pipe is longitudinally fixed relative to the body.

8. The instrument of claim 6, wherein the distal tip of the electrode has a first position corresponding to the extended position of the electrode and a second position corresponding to the withdrawn position of the electrode, in the first position the distal tip extends radially outwardly beyond the outer dimension of the suction pipe and in the second position the distal tip is positioned within the lumen of the suction pipe.

9. An electrosurgical instrument comprising:
a body having a nose positioned at a distal end of the body, the nose including a central passage defining a longitudinal axis, the body defining a longitudinal slot in an outer surface of the body;
an activation switch fixed within the longitudinal slot of the body;
a suction pipe having a distal end and disposed within the body;
an electrode having a distal tip, the electrode disposed within the body and configured to deliver energy to tissue, the electrode slidable along the longitudinal axis with respect to the body; and
an actuating member operably coupled to the electrode and configured to move the electrode between a withdrawn position, wherein the distal tip of the electrode is positioned within the body proximal to the distal end of the body, and an extended position, wherein at least a portion the distal tip of the electrode extends distally from the distal end of the body, wherein in the extended position of the electrode the actuating member is configured to engage the activation switch to activate delivery of energy from the electrode to tissue.

10. The instrument of claim 9, wherein the body includes a chamber positioned at a proximal end of the central passage, the chamber in fluid connection with the distal end of the body, and the instrument further includes an irrigation pipe having a distal end, the distal ends of the suction pipe and the irrigation pipe positioned at and in fluid connection with the chamber.

11. The instrument of claim 10, wherein the distal end the suction pipe includes a directional valve configured to permit fluid to flow from the chamber to the suction pipe and configured to inhibit fluid from flowing from the suction pipe to the chamber.

12. The instrument of claim 10, wherein the distal end of the irrigation pipe includes a directional valve configured to permit fluid to flow from the irrigation pipe to the chamber and configured to inhibit fluid from flowing from the chamber to the irrigation pipe.

* * * * *